United States Patent [19]

McKenna

[11] Patent Number: 4,892,479
[45] Date of Patent: Jan. 9, 1990

[54] ORTHODONTIC ARCH WIRE

[76] Inventor: John C. McKenna, 39 Stoner Dr., West Hartford, Conn. 06107

[21] Appl. No.: 255,495

[22] Filed: Oct. 11, 1988

[51] Int. Cl.⁴ .............................................. A61C 3/00
[52] U.S. Cl. ..................................................... 433/20
[58] Field of Search ......................................... 433/20

[56] References Cited

U.S. PATENT DOCUMENTS

| | | | |
|---|---|---|---|
| 1,014,028 | 1/1912 | Angle | 433/10 |
| 2,566,414 | 9/1951 | Henry | 433/20 |
| 3,043,007 | 7/1962 | Wallshein | 433/20 |
| 3,374,542 | 3/1968 | Moylan | 433/20 |
| 3,505,736 | 4/1970 | Brader et al. | 433/20 |
| 3,906,634 | 9/1975 | Aspel | 433/24 |
| 4,384,851 | 5/1983 | McAndrews | 433/7 |
| 4,408,989 | 10/1983 | Cleary | 433/7 |
| 4,571,179 | 2/1986 | Balenseifen | 433/20 |
| 4,592,725 | 6/1986 | Goshgarian | 433/7 |
| 4,637,796 | 1/1987 | Korn | 433/7 |
| 4,764,112 | 8/1988 | Bergersen | 433/20 |

*Primary Examiner*—John J. Wilson
*Attorney, Agent, or Firm*—Chilton, Alix & Van Kirk

[57] ABSTRACT

An orthodontic arch wire is provided with a mid-point marker in the form of a displacement dimple offset from the principal plane of the wire at its center line. The dimple cooperates with adjacent brackets to restrict sideways displacement of the wire.

10 Claims, 2 Drawing Sheets

ORTHODONTIC ARCH WIRE

BACKGROUND AND SUMMARY OF THE INVENTION

The present invention relates to orthodontics and is more particularly concerned with a new and improved orthodontic arch wire that is used as the force imparting component in orthodontic appliances.

In the field of orthodontics, a force imparting wire is used to correct irregularities and/or abnormalities in the relationship between various teeth within the dental arch. The wires are elastically deformed and absorb and release energy during loading and unloading so as to provide a force magnitude that will rapidly and relatively painlessly move the teeth with minimum tissue damage. The wire applies a constant force level over time in order to provide appropriate tooth movement with maximum tissue response. Thus, as can be appreciated, in order to provide proper and effective treatment, it is necessary to position or locate the arch wire accurately on the patient for maximum effective treatment.

Arch wires are frequently preformed and provided with a marking at the mid-point of the wire to assist in locating the wire on the patient. This marking typically consists of a spot of ink or vegetable dye that has been FDA-approved for that use. However, the dye is not permanent, is easily removed and frequently wears off or is wiped off as the arch wire is being applied to the patient. Additionally, the vegetable dye is typically light in color and difficult to identify. Thus, it is quite easy for the arch wire to be placed on the patient in an inaccurate position. This mispositioning of the wire can be further aggravated if the wire tends to slide from side to side during mounting or adjustment and, under such conditions, the posterior sections of the wire may be displaced by an extent sufficient to even injure the patient.

In accordance with the present invention, it has been found that the mid-point can be permanently, visibly, and accurately designated on the wire in such a way that it not only can be readily observed by the orthodontist but will facilitate removal and precise remounting of the wire if such is needed for necessary adjustments. This is achieved in accordance with the present invention by providing a visible, tactilely discernable arch wire mid-point indicator that is not only easily identified, but will resist or limit excessive sideways movement thereby avoiding the possibility for slidable mispositioning and the requirement for repositioning the wire. Accurate positioning in turn reduces the office time of the patient and permits the orthodontist to proceed rapidly with the appropriate adjustment of the wire on the patient. These results are achieved without adversely impacting the primary functional characteristics of the arch wire while simultaneously assuring repeatedly accurate positioning thereof.

Other features and advantages of the present invention will be in part obvious and in part pointed out more in detail hereinafter.

These and related features are achieved in accordance with the present invention by providing an orthodontic arch wire of uniform longitudinal cross-section curved in a generally U-shaped configuration. This curved arch defines both a principal plane of the wire as well as a center line for the arch within the plane. In accordance with the present invention, the arch wire is provided at its center line with a mid-point indicator in the form of a displaced wire portion such as a wire segment or dimple that is offset from the principal plane of the arch wire but does not disrupt the continuous radial curvature of the arch wire at its center line and at the wire segments immediately adjacent thereto.

The displaced wire portion at the center of the arch wire extends outwardly above the plane of the wire only a very slight distance, which distance is sufficient to cooperate with brackets mounted on the patient's central incisors so as to impede movement of the displaced portion past the mesial portion of the central incisor brackets. Since the mid-point marker is offset from the plane of the wire by only a slight degree, it performs no function with respect to the movement of the teeth and provides no adverse impact on the shape of the arch wire. However it does clearly limit the sliding movement of the wire within the arch without altering the thickness or cross-section of the wire at the mid-point.

A better understanding of the invention will be obtained from the following detailed description and the accompanying drawings of illustrated applications of the invention wherein the features, properties and relation of element are described and exemplified.

DESCRIPTION OF A PREFERRED EMBODIMENT

Figure 1:
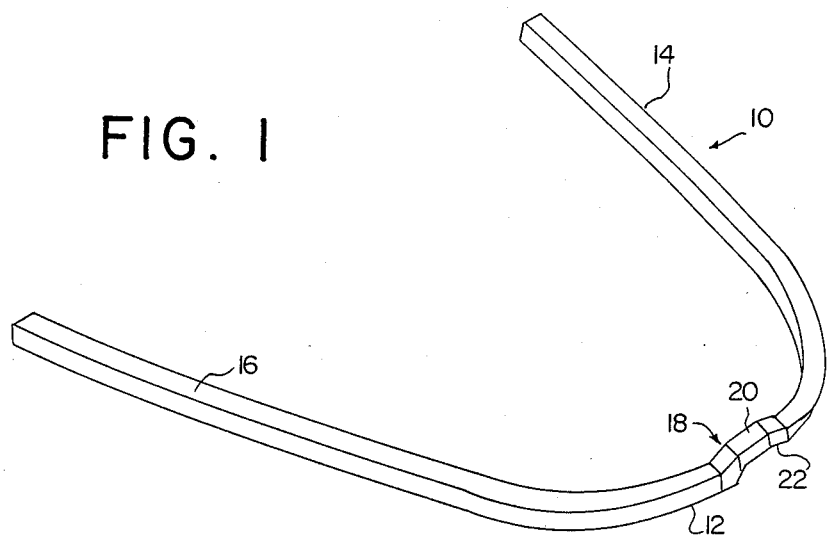
FIG. 1 is a perspective view of the arch wire of the present invention.

Referring now to the drawings in greater detail wherein like reference numerals indicate like parts throughout the several figures, the present invention is shown as being incorporated within an arch wire 10 that is conventional in every respect accept for the mid-point area thereof. In the particular embodiment illustrated, the arch wire 10 is of square cross section. However, as can be appreciated, the particular cross section of the wire is not a critical feature of the present invention and various cross sectional configurations can be employed.

Figure 3:
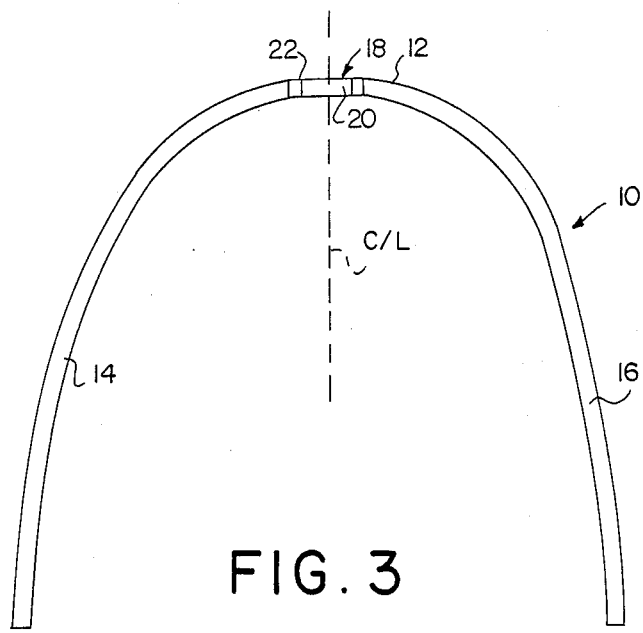
FIG. 3 is a top plan view of the arch wire of FIG. 1.

Arch wires are typically preformed into the generally U-shaped configuration illustrated in FIG. 1 and are adjustably contoured by the orthodontist at the time the wire is fitted to the patient's dental arch. As shown, the wire 10 consists of a central arcuate portion 12 and a pair of relatively straight terminal portions 14 and 16 attached to opposite ends of the central portion 12. This unitary structure is of substantially uniform cross-section throughout its length and lies almost entirely within a single flat plane. As shown in FIG. 3, the wire 10 typically is symmetrical about its center line, C/L, that extends through the arcuate central portion 12 thereof. Although the mid-point of an arch wire is not always indicated, preformed arch wires typically have been marked by a vegetable dye or ink at the mid-point thereof to facilitate accurate placement of the wire on the patient. A mid-point marking dye or ink must be FDA-approved but has the disadvantage that it can easily be removed in general handling in the orthodontist's office. Additionally, the ink mid-point indicator is very light in color and difficult to read. In fact, as a result of wiping or rubbing, the mid-line may become essentially invisible upon insertion into the patient's mouth, particularly under the reflected glare from the arch wire and other orthodontic appliances within the patient's mouth.

In accordance with the present invention, it has been found that the foregoing disadvantages can be overcome by incorporating into the arch wire a permanent mid-point indicator or marker that is visible, permanent and tactilely discernable. Such an indicator enhances identification of the mid-point and at the same time prevents the arch wire from sliding excessively toward one side or the other. This is achieved, as shown in the drawings, by incorporating into the wire a displacement dimple 18 at the center line of the wire As best seen in FIG. 3, the dimple 18 need not, and preferably should not, in any way alter the smooth arcuate curvature of the central portion 12 of the arch wire or shape the arch form so as to adversely impact the operative characteristics of the wire Of course, as can be appreciated, the displacement dimple may extend perpendicularly from the plane of the arch wire or tilt slightly, for example in a gingival direction, or exhibit other contour characteristics without departing from the spirit and scope of the invention.

Figure 2:
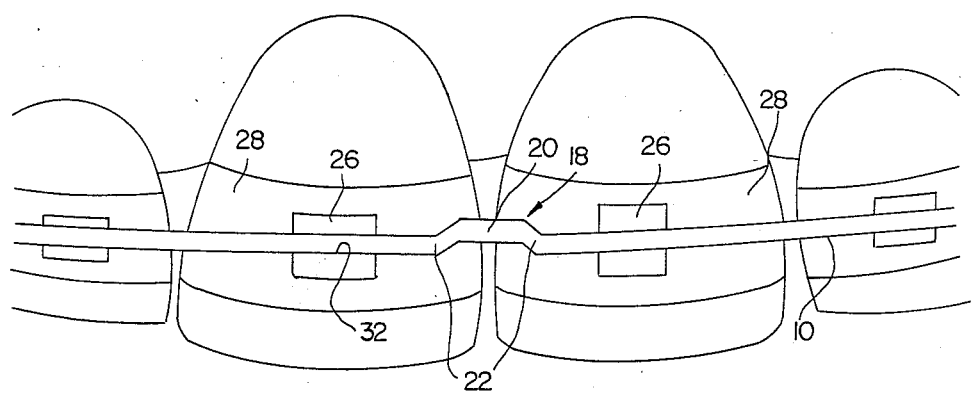
FIG. 2 is an enlarged front elevational view of the mid-point area of arch wire mounted within brackets on a patient's maxillary denture.

In the embodiment illustrated in FIGS. 1-3, the displacement dimple 18 takes the form of a generally flat central segment 20 that is raised above but parallel to the plane of the arch wire. As best shown in FIG. 2, the central segment 20 remains parallel to the remainder of the wire but is offset therefrom by a distance equal to about one half the thickness of the wire. Although the degree of displacement or offset may vary, it primarily should be to an extent that will cause sliding interference with the adjacent central incisor brackets so as to limit or restrict sideways movement of the arch wire within the mouth of the patient. Since the wire-receiving notch in the bracket typically has a dimension that is about 0.002-0.006 inch larger than the thickness of the wire inserted therein, the displacement dimple should be offset from the plane of the arch wire by at least that distance and preferably slightly greater. In this connection, a dimple having an offset of at least 0.008 inch is typically employed, with the optimum offset being about 0.010-0.012 inch.

Additionally, since the displacement dimple 18 is not designed to alter the shape or form the arch or in any way apply force components sufficient to move teeth in any particular direction, it is preferred that the dimple be constructed in such a way as to essentially maintain the integrity of the cross-section of the wire throughout the dimple area. In other words, the dimple should not severely constrict the thickness of the wire at or adjacent the mid-point of the wire. Rather, it should maintain substantially the same cross-section as the wire immediately adjacent both ends of the dimple. Thus, as shown in the drawing, the flat offset or displaced central segment 20 of the dimple 18 is connected to the remainder of the arch wire through sloping connecting portions 22 that are substantially the same size as both the central segment 20 and the immediately adjacent connecting portions of the arch wire's central section 12. These connecting portions 22 are relatively short in length to assure the desired interferring engagement with the adjacent brackets.

As shown in FIG. 2, brackets 26 or other wire-mounting devices are typically attached to the patient's teeth such as by individual bands 28 encircling each tooth or by adhesively secured pads 30 (FIG. 4) or other attachment devices. Each bracket 26 is shown as being provided with a wire-receiving slot or notch 32 that typically is of the same cross-sectional configuration as the arch wire but may be slightly larger than the wire to facilitate ease of mounting As will be appreciated, any conventional bracket, tube or other mounting member may be employed in connection with the arch wire of the present invention.

Figure 4:
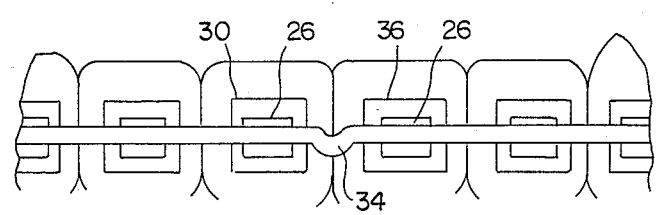
FIG. 4 is a front elevational view of the mid-point area of the arch wire showing another embodiment of the mid-point marker, the wire being mounted on a mandibular denture.

The particular configuration of the displacement dimple may vary significantly so long as it provides the primary beneficial features noted hereinbefore, such as the permanent non-movable mid-point indicator that is easily identifiable and does not adversely impact on the functional performance of the arch wire. Additionally, as mentioned, in the preferred embodiment the displacement dimple is offset by a distance sufficient to impede movement of the arch wire past the mesial portion of the central incisor brackets. The maximum degree of offset as well as the configuration of the dimple is, of course, controlled by both aesthetics and comfort to the patient. In this connection, it will be appreciated that the mid-point marker may symmetrically straddle the centerline of the wire as shown or may be predominantly on one side thereof so as to abut the adjacent bracket FIG. 4 illustrates another embodiment of the mid-point indicator of the present invention mounted on the mandibular denture. In that embodiment, the dimple 34 is of significantly shorter longitudinal extent and essentially eliminates the flat central segment 20 of the dimple 18 shown in FIG. 1. Although the dimples 18 and 34 extend in the gingival direction in both FIGS. 2 and 4, it will be appreciated that the dimple may extend in either the gingival or the incisal direction without causing significant discomfort to the patient and yet still provide all of the aforementioned features and advantages.

The mid-point marker of the present invention can be employed with a wide variety of arch wire materials. For example, it may be incorporated into arch wires made from the conventional 18-8 stainless steel or from the newer, more flexible alloys, such as the nickel titanium alloys sold under the name "Nithinol", as described in U.S. Pat. Nos. 3,351,463 and 4,037,324 as well as the beta titanium alloys described in U.S. Pat. No. 4,197,643.

As can be seen from the foregoing detailed description, the mid-point indicator of the present invention enhances and facilitates the identification of the wire's center line by providing not only a visible indicator but also one that is tactilely discernable, non-erasable and permanently positioned. This indicator can easily be formed at the time of initially forming the arch and at little or no additional expense. It prevents the arch wire from sliding or moving sideways by cooperating with the adjacent central incisor brackets to severely restrict sideways movement thereof. The orthodontist is assured that upon mounting of the arch wire on the patient by either the doctor or by auxiliary personnel, its placement will remain substantially constant, eliminating mispositioning of the arch wire in the patient's mouth. The mid-point indicator may take various forms and configurations but should not be offset from the plane of the dental arch to a degree that would adversely impact on the primary functioning of the arch wire, i.e. applying the desired corrective forces to the denture of the patient.

As will be apparent to a person skilled in the art, various modifications, adaptations, and variations of the foregoing disclosure can be made without departing from the teachings of the present invention.

What is claimed is:

1. In an orthodontic arch wire used with anterior brackets comprising a wire of uniform cross-section along its length having a generally U-shaped configuration and defining both a principal plane of the arch wire and center line for the arch within the plane, the improvement wherein the wire is provided with a mid-point marker in the form of a displaced wire portion offset from the principal place of the arch wire at the center line, said displaced offset including a pair of integral inclined portions connecting the offset to the remainder of the wire, the ends of said inclined portions connected to the remainder of the wire defining a gap therebetween within the plane of the wire, said offset being spaced from the wire by up to about 0.012 inch and being insufficient to substantially alter the continuous radial curvature of the arch wire at the center line or to apply force components to the wire.

2. The arch wire of claim 1 wherein the displaced wire portion is offset from the plane of the arch wire to an extend sufficient to provide interference with an adjacent wire attachment for preventing excessive sideway sliding movement of the wire.

3. The arch wire of claim 1 wherein the displaced wire portion is in the form of a dimple extending out of the plane of the wire.

4. The arch wire of claim 1 wherein the displaced wire portion is offset from the plane by at least 0.002 inch.

5. The arch wire of claim 1 wherein the offset is at least about 0.008 inch.

6. The arch wire of claim 1 wherein the displaced wire portion extends perpendicularly to the plane of the arch wire.

7. In an orthodontic arch wire comprising a wire of uniform cross-section along its length having a generally U-shaped configuration and defining both a principal plane of the arch wire and center line for the arch within the plane, the improvement wherein the wire is provided with a mid-point marker in the form of a displaced wire portion offset from the principal plane of the arch wire at the center line, the displaced wire portion including a central segment offset from and substantially parallel to the plane of the wire and a pair of integral inclined portions connecting the segment to the remainder of the wire, said offset being insufficient to substantially alter the continuous radial curvature of the arch wire at the center line of adversely impact the operative characteristic of the wire.

8. The arch wire of claim 1 wherein the displaced wire portion is arcuately contoured.

9. A method of forming an orthodontic arch wire used with anterior brackets with a permanent mid-point marker comprising the steps of providing a wire having a generally U-shaped configuration and defining both a principal plane of an arch wire and a center line for the arch within the plane and displacing a portion of the wire from the principal plane thereof at said center line, said displacement being insufficient to substantially alter the continuous radial curvature of the arch wire at the center line or to apply force components to the wire but being sufficient to provide interference with a wire attachment for preventing excessive sideway sliding movement of the wire.

10. The method of claim 9 wherein the displacement is in the form of a tactilely discernible dimple extending out of the plane of the wire.

* * * * *